(12) United States Patent
Schoenle et al.

(10) Patent No.: US 7,541,077 B2
(45) Date of Patent: *Jun. 2, 2009

(54) MEDICAL DEVICE COMPONENTS

(75) Inventors: Victor Schoenle, Greenfield, MN (US); Daniel James Horn, Shoreview, MN (US); Yiqun Wang, Tokyo (JP); Lixiao Wang, Long Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/929,208

(22) Filed: Oct. 30, 2007

(65) Prior Publication Data

US 2008/0051760 A1    Feb. 28, 2008

Related U.S. Application Data

(63) Continuation of application No. 10/669,059, filed on Sep. 23, 2003, which is a continuation-in-part of application No. 10/256,612, filed on Sep. 26, 2002, now Pat. No. 7,323,233.

(51) Int. Cl.
*B32B 1/08* (2006.01)
*F16L 11/04* (2006.01)
*F16L 11/20* (2006.01)
*A61M 29/02* (2006.01)
*A61M 39/00* (2006.01)

(52) U.S. Cl. .............. 428/36.9; 428/34.1; 428/35.2; 428/35.7; 428/36.91; 604/19; 604/96.01

(58) Field of Classification Search ............... 428/34.1, 428/35.2, 35.5, 35.7, 36.1, 36.9, 36.91, 36.92; 604/19, 48, 93.01, 96.01
See application file for complete search history.

(56) References Cited

U.S. PATENT DOCUMENTS

| 3,027,487 | A | | 3/1962 | Dench |
| 3,356,108 | A | | 12/1967 | Johnston |
| 3,406,685 | A | | 10/1968 | May |
| 3,861,972 | A | | 1/1975 | Glover et al. |
| 3,969,176 | A | | 7/1976 | Bassett et al. |
| 4,418,189 | A | | 11/1983 | Morello |
| 4,695,280 | A | * | 9/1987 | Watanabe et al. .......... 623/1.54 |
| 5,306,246 | A | | 4/1994 | Sahatjian et al. |

(Continued)

FOREIGN PATENT DOCUMENTS

WO    WO99/44649    10/1999

OTHER PUBLICATIONS

International Search Report dated Jan. 30, 2004 for PCT/US03/29922.

*Primary Examiner*—Rena L Dye
*Assistant Examiner*—Walter B Aughenbaugh
(74) *Attorney, Agent, or Firm*—Crompton, Seager & Tufte, LLC

(57) ABSTRACT

Medical device components, such as tube-shaped catheter components, are disclosed. In some embodiments, a medical device component includes a region that includes a polyamide having a post buckle fracture tensile strength of at least about 6500 psi.

15 Claims, 5 Drawing Sheets

U.S. PATENT DOCUMENTS

| | | |
|---|---|---|
| 5,439,447 A | 8/1995 | Miraki |
| 5,496,275 A | 3/1996 | Sirhan et al. |
| 5,690,613 A | 11/1997 | Verbeek |
| 5,860,998 A | 1/1999 | Robinson et al. |
| 6,027,487 A | 2/2000 | Crocker |
| 6,110,142 A * | 8/2000 | Pinchuk et al. .......... 604/96.01 |
| 6,124,007 A * | 9/2000 | Wang et al. ............... 428/35.2 |
| 6,200,290 B1 * | 3/2001 | Burgmeier ............... 604/96.01 |
| 6,238,376 B1 | 5/2001 | Peterson |
| 6,240,231 B1 | 5/2001 | Ferrera et al. |
| 6,257,800 B1 | 7/2001 | Masters |
| 6,280,545 B1 | 8/2001 | Kanesaka |
| 6,322,586 B1 | 11/2001 | Monroe et al. |
| 6,352,531 B1 | 3/2002 | O'Connor et al. |
| 7,323,233 B2 * | 1/2008 | Horn et al. ................. 428/36.9 |
| 2004/0062891 A1 | 4/2004 | Horn et al. |

* cited by examiner

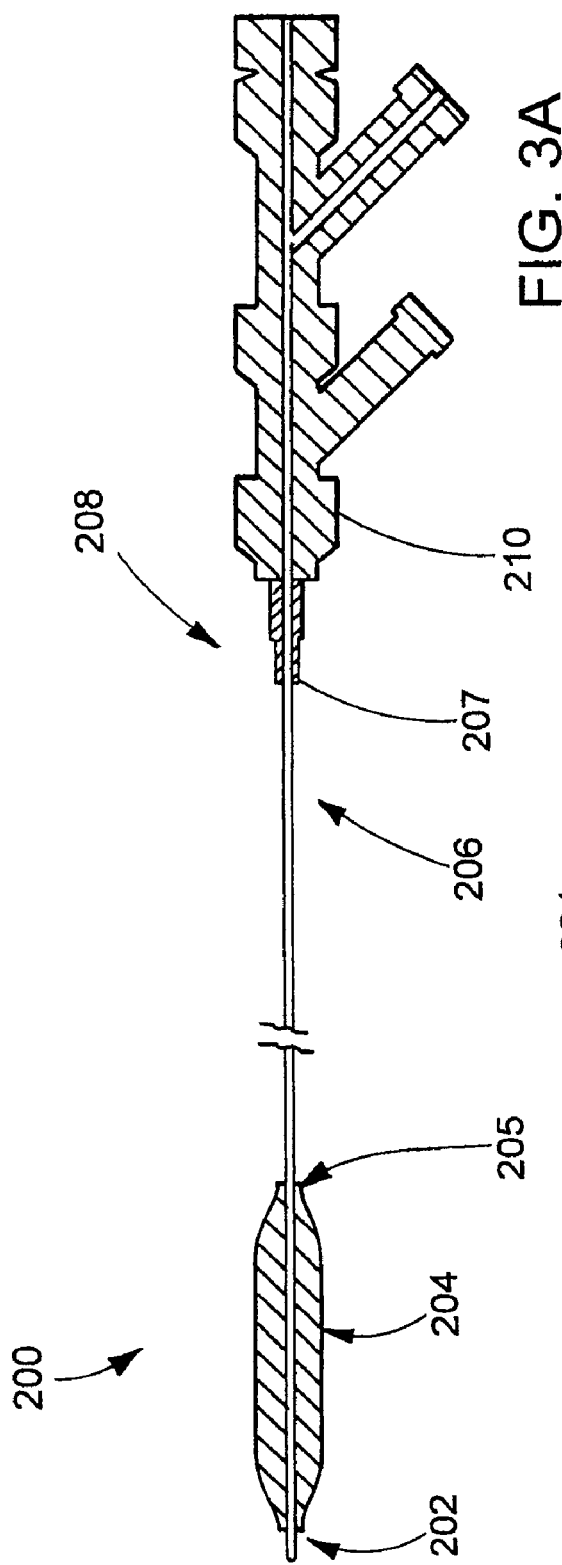
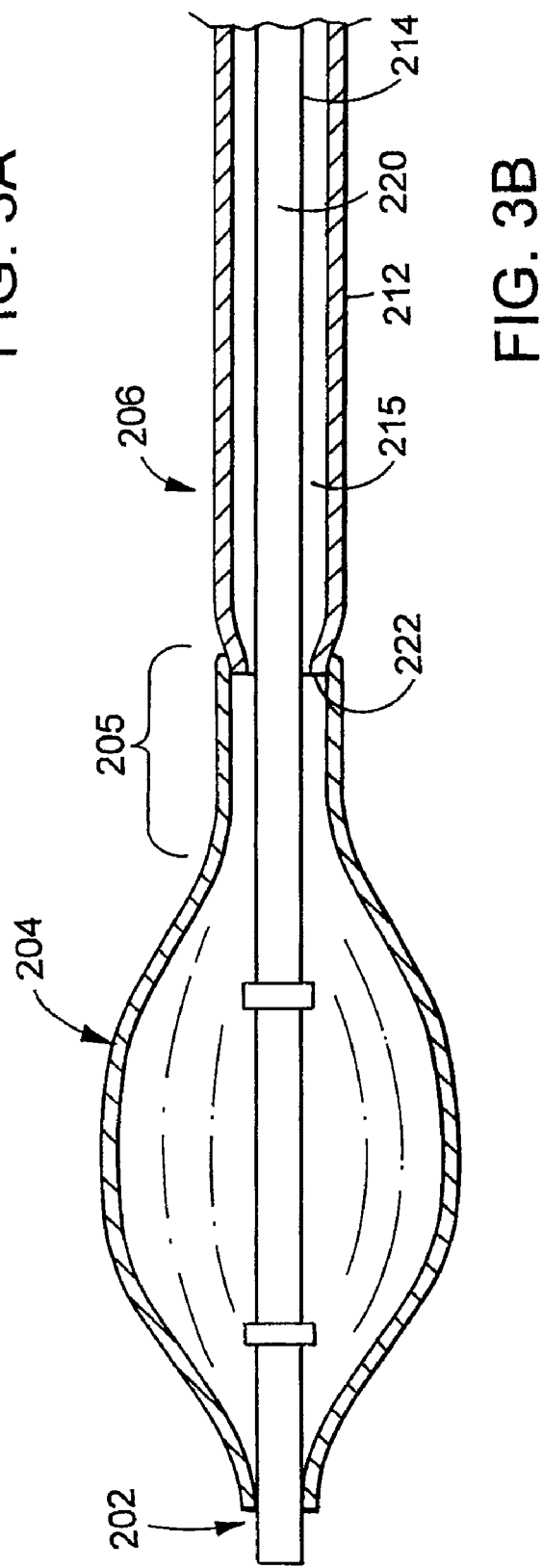

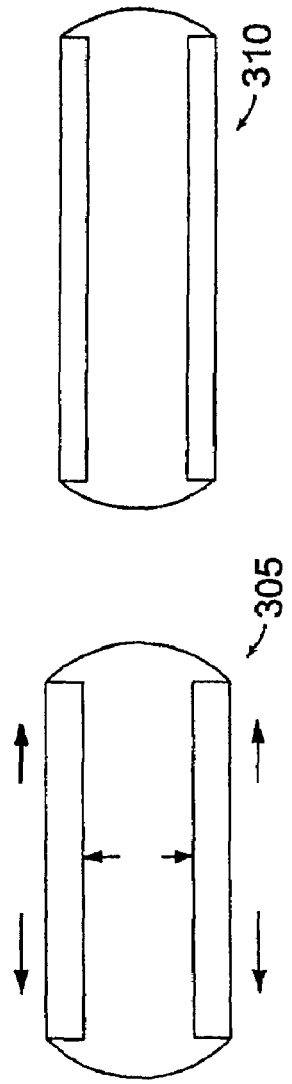
FIG. 4A
FIG. 4B
FIG. 4C
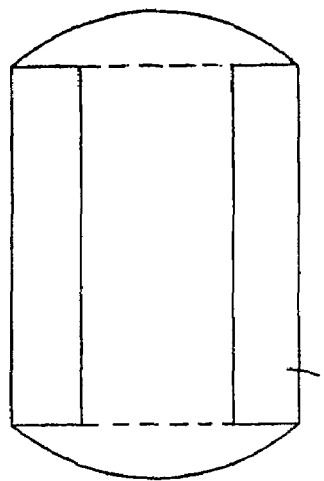
FIG. 4D
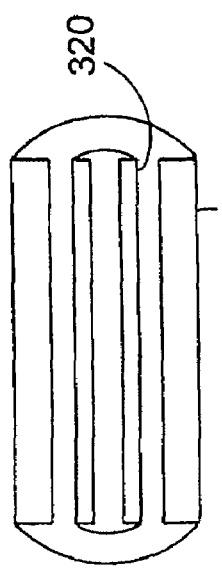
FIG. 4E

MEDICAL DEVICE COMPONENTS

CLAIM OF PRIORITY

This application is a continuation of, and claims priority under 35 U.S.C. § 120 to, and commonly owned U.S. patent application Ser. No. 10/669,059, filed on Sep. 23, 2003 and entitled "Medical Device Components and Processes," which is a continuation-in-part of, and claims priority under 35 U.S.C. § 120 to, and commonly owned U.S. patent application Ser. No. 10/256,612, filed on Sep. 26, 2002, now U.S. Pat. No. 7,323,233, and entitled "Sheath Materials and Processes." The entire contents of each of the above-noted applications is incorporated by reference herein.

TECHNICAL FIELD

The invention relates to medical device components, such as tube-shaped catheter components.

BACKGROUND

Medical device components (e.g., tube-shaped catheter components) are used in a variety of systems.

For example, tube-shaped catheter components can be used in balloon catheters. Balloon catheters are commonly used in medical procedures. As an example, in some procedures a balloon catheter is used to open an occluded lumen, as in angioplasty. As another example, a balloon catheter can be used to selectively block a passageway. In additional examples, a balloon catheter is used in various combinations of these procedures. Typically, the procedures include positioning a balloon catheter within a blood vessel at a location of treatment, and inflating the balloon portion of the catheter with an inflation fluid. The balloon is then deflated and the catheter is withdrawn from the body.

As another example, tube-shaped catheter components can be used in systems for delivering medical devices, such as stents or grafts. The medical devices can be balloon-expandable or self-expanding.

SUMMARY

The invention relates to medical device components, such as tube-shaped catheter components.

In one aspect, the invention features a method of making a component of a medical device. The method includes longitudinally stretching a tube-shaped article while heating the tube-shaped article and pressurizing an interior of the tube-shaped article to form the component of the medical device.

In another aspect, the invention features a method of making a tube-shaped component of a medical device. The method includes heating a tube-shaped article while pressurizing an interior of the tube-shaped article to form the tube-shaped component of the medical device.

In another aspect, the invention features a component (e.g., a catheter) of a medical device. The component includes a polymer with a tensile strength of at least about 21,000 psi (e.g., at least about 22,500 psi).

In another aspect, the invention features a tube-shaped portion of a catheter. The tube-shaped portion has a tensile strength of at least about 21,000 psi (e.g., at least about 22,500 psi).

In another aspect, the invention features a component (e.g., a catheter) of a medical device. The component includes a polymer with a hoop stress of at least about 3300 psi (e.g., at least about 3500 psi).

In another aspect, the invention features a tube-shaped portion of a catheter. The tube-shaped portion has a hoop stress of at least about 3300 psi (e.g., at least about 3500 psi).

In another aspect, the invention features a tube-shaped portion of a catheter. The tube-shaped portion has a load at break ratio of at least about 1.25 (e.g., at least about 1.5).

In another aspect, the invention features a component (e.g., a catheter) of a medical device. The component includes a polymer with a load at break ratio of at least about 1.25 (e.g., at least about 1.5).

In another aspect, the invention features a component (e.g., a catheter) of a medical device. The component includes a polymer having a hoop stress ratio of at least about 1.25 (e.g., at least about 1.5).

In another aspect, the invention features a tube-shaped portion of a catheter. The tube-shaped portion has a hoop stress ratio of at least about 1.25 (e.g., at least about 1.5).

In another aspect, the invention features a component (e.g., a catheter) of a medical device. The component includes a polymer with a post buckle fracture tensile strength of at least about 6500 psi.

In another aspect, the invention features a tube-shaped portion of a catheter. The tube-shaped portion has a post buckle fracture tensile strength of at least about 6500 psi.

Embodiments can include one or more of the following.

While longitudinally stretching the tube-shaped article and/or pressurizing the interior of the tube-shaped article, the tube-shaped article can be heated to a temperature that is at least about 0.85 times a glass transition temperature of the tube-shaped article.

While longitudinally stretching and/or heating the tube-shaped article, a pressure in the interior of the tube-shaped article can be at least about 50 psi.

While longitudinally stretching the tube-shaped article, a longitudinal strain of the tube-shaped article can be at least about 110%.

The method can further include longitudinally stretching a second tube-shaped article while heating the second tube-shaped article and pressurizing an interior of the second tube-shaped article to form a second component of the medical device. The method can also include joining the two components of the medical device.

The method can further include heating a second tube-shaped article while pressurizing an interior of the second tube-shaped article to form a second tube-shaped component of the medical device. The method can also include joining the two tube-shaped components of the medical device.

The tube-shaped article and/or the component can include a polymer.

The tube-shaped article can include a first section and a second section.

The method can include longitudinally stretching the first section while heating the first section and pressurizing an interior of the first section, without longitudinally stretching the second section.

The method can include heating the first section while pressurizing an interior of the first section, without radially stretching the second section.

The component can be tube-shaped. The component can be a catheter.

The medical device can be a catheter.

The catheter can have, for example, a length of from about 30 centimeters to about 180 centimeters, and/or an outer diameter of from about 0.020 inch to about 0.180 inch.

The medical device can be a balloon catheter. The balloon catheter can include a coronary balloon, an aortic balloon, a peripheral balloon, a reperfusion balloon, an endoscopy balloon, a urology balloon, or a neurology balloon.

The medical device can be a catheter that is configured to deliver an endoprosthesis (e.g., a self-expanding stent, a balloon-expandable stent) to a body vessel.

The component can be a hypotube sheath portion of a catheter. The hypotube sheath portion can have a length of from about 0.100 inch to about 60 inches and/or an outer diameter of from about 0.015 inch to about 0.180 inch.

The component can be a midshaft portion of a catheter. The midshaft portion can have a length of from about four centimeters to about 25 centimeters, and/or an outer diameter of from about 0.015 inch to about 0.180 inch.

The component can be a distal outer portion of a catheter. The distal outer portion can have a length of from about ten centimeters to about 40 centimeters, and/or an outer diameter of from about 0.015 inch to about 0.180 inch.

The component can be a distal inner portion of a catheter. The distal inner portion can have a length of from about ten centimeters to about 40 centimeters, and/or an outer diameter of from about 0.015 inch to about 0.180 inch.

A wall thickness of the component can be less than a wall thickness of the tube-shaped article.

An outer diameter of the component can be less than an outer diameter of the tube-shaped article.

An inner diameter of the component can be less than an inner diameter of the tube-shaped article.

The component, the polymer, and/or the tube-shaped portion can have a tensile strength of at least about 21,000 psi (e.g., at least about 22,500 psi).

The component, the polymer, and/or the tube-shaped portion can have a post buckle fracture tensile strength of at least about 6500 psi (e.g., at least about 8000 psi).

The component, the polymer, and/or the tube-shaped portion can have a hoop stress of at least about 3300 psi (e.g., at least about 3500 psi).

The component, the polymer, and/or the tube-shaped portion can have a hoop stress ratio of at least about 1.25 (e.g., at least about 1.5).

The component, the polymer, and/or the tube-shaped portion can have a load at break ratio of at least about 1.25 (e.g., at least about 1.5).

The tube-shaped article can include at least one layer. The at least one layer can include a polymer.

The tube-shaped article can include at least two layers.

The tube-shaped article can have a first layer including a first polymer and a second layer including a second polymer. The first polymer can be different from the second polymer.

The at least two layers can be coextruded and/or joined by an adhesive.

The component and/or the tube-shaped portion can have a first layer and a second layer, and the first layer can have a different flexibility from the second layer.

Features and advantages are in the description, drawings, and claims.

DESCRIPTION OF DRAWINGS

FIG. 3A is a side view of another embodiment of a balloon catheter.

FIG. 3B is a cross-sectional view of the distal end of the balloon catheter of FIG. 3A.

FIGS. 4A-4E are cross-sectional views of an embodiment of a process for forming a tube-shaped catheter component.

DETAILED DESCRIPTION

Figure 1:
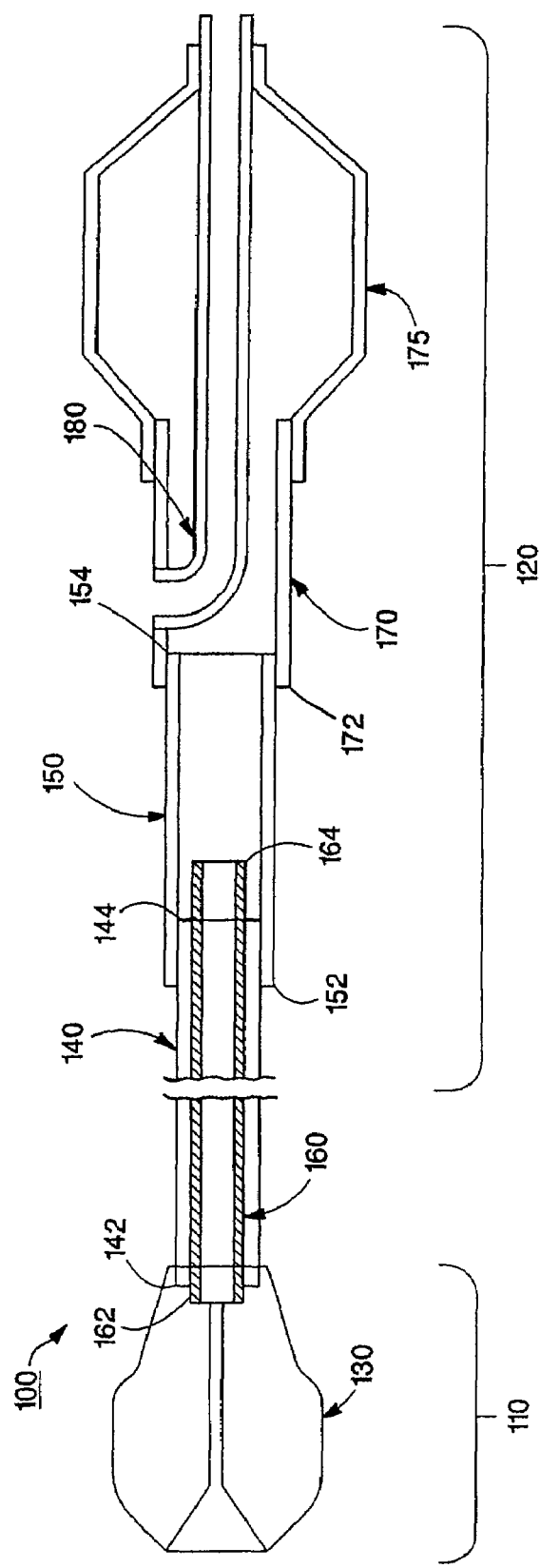
FIG. 1 is a cross-sectional view of an embodiment of a balloon catheter.

FIG. 1 is a cross-sectional view of a balloon catheter 100 having a proximal end 110, which generally remains outside the body, and a distal end 120. A manifold 130 is connected to the balloon catheter at proximal end 110. Balloon catheter 100 further includes a sheath 140 having proximal end 142 and distal end 144, a midshaft 150 having a proximal end 152 and a distal end 154, a hypotube 160 having a proximal end 162 and a distal end 164, a distal outer 170 having a proximal end 172, a distal inner 180, and a balloon 175. Sheath 140 surrounds and is bonded to a portion of hypotube 160. Sheath 140 is also bonded to midshaft 150, and midshaft 150 is also bonded to distal outer 170. Balloon catheters having this general configuration are known. Examples of such commercially available balloon catheters include the Monorail™ family of balloon catheters (Boston Scientific-SciMed, Maple Grove, Minn.).

Typically, balloon catheter 100 is used as follows. An operator of balloon catheter 100 delivers distal end 120 of balloon catheter 100 into a body lumen (e.g., a blood vessel) over a guidewire. Balloon catheter 100 is threaded through the lumen to position balloon 175 at the site of an occlusion. Once balloon 175 reaches the occlusion, balloon 175 is inflated with inflation fluid, so that balloon 175 presses against the occlusion. Thereafter, balloon 175 is deflated and removed from the lumen. Alternatively or additionally, balloon 175 can be used to deliver a medical device (e.g., a stent, a graft) and/or to block a passageway.

Manifold 130 is generally designed to control the delivery of inflation fluid to balloon 175, and to control the positioning of distal end 120 of balloon catheter 100 in a lumen.

In general, hypotube 160 is designed to act as a part of the conduit for the inflation fluid and to impart an appropriate amount of stiffness to balloon catheter 100 so that balloon catheter 100 can be positioned (e.g., in a blood vessel) within a patient. Hypotube 160 is typically made of a metal or an alloy, although in some cases hypotubes can be made of a polymer (e.g., one or more of the polymers discussed below). Examples of alloy hypotube materials include nitinol and stainless steel (e.g., 303, 304, 316L).

Generally, sheath 140 is designed to reinforce hypotube 160. Sheath 140 typically is formed of a material that is relatively thin and/or relatively strong (e.g., a material having a relatively high tensile strength and/or a relatively high hoop stress). Sheath 140 can be formed, for example, of a polymer (e.g., one or more of the polymers discussed below).

Midshaft 150 is generally designed to act as an additional portion of the conduit for the inflation fluid, and to provide balloon catheter 100 with a region of intermediate flexibility. Midshaft 150 is typically made of a material that is softer and/or more flexible than the material from which hypotube 160 is formed. Typically, midshaft 150 has a Shore D hardness of about 72 or more. Midshaft 150 can be formed, for example, of a polymer (e.g., one or more of the polymers discussed below).

Generally, distal outer 170 is designed to act as an additional portion of the conduit for the inflation fluid. Distal outer 170 is typically made of a material that is softer and/or more flexible than the material from which midshaft 150 is formed. Typically, distal outer 170 has a Shore D hardness of about 70 or less. Distal outer 170 can be formed, for example, of a polymer (e.g., one or more of the polymers discussed below).

Distal inner 180 is generally designed to house a guidewire. In some embodiments, distal inner 180 is made of a material that is harder than the material from which distal outer 170 is formed, while in other embodiments distal inner 180 is made of a material that is softer than the material from which distal outer 170 is formed. The Shore D hardness of distal inner 180 can be less than, the same as, or more than the Shore D hardness of distal outer 170. Distal inner 180 generally is strong enough to withstand pressure from inflation fluid. Distal inner 180 can be formed, for example, of a polymer (e.g., one or more of the polymers discussed below).

The guidewire is typically formed of a metal or alloy and is used to provide the appropriate amount of stiffness to balloon catheter 100 while it is being positioned within a body lumen. A portion of the guidewire is disposed within distal inner 180, and a portion of the guidewire is disposed along the outer surface of midshaft 150 and sheath 140 (e.g., so that this portion of the guidewire is disposed inside of a guide catheter surrounding distal end 120 of balloon catheter 100).

Balloon 175 can be made of any material appropriate for use in the balloon of a balloon catheter. Typically, balloon 175 is made of one or more layers of polymeric materials. Typical polymeric materials include polyesters and polyamides. Exemplary materials are disclosed, for example, in U.S. Published Patent Application No. US 2002/0165523 A1, published on Nov. 7, 2002, and entitled "Multilayer Medical Device," which is hereby incorporated by reference.

Figure 2:
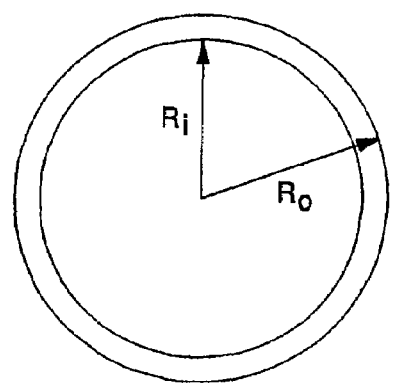
FIG. 2 is a cross-sectional view of an embodiment of a tube-shaped catheter component.

Referring to FIG. 2, a tube-shaped catheter component (e.g., sheath 140, hypotube 160, midshaft 150, distal outer 170, or distal inner 180) has an inner radius ($R_i$), an outer radius ($R_o$), and a wall thickness ($R_o - R_i$).

The tube-shaped catheter component can be used in any of a number of different applications including, for example, coronary (e.g., 0.014 inch wire systems), peripheral (e.g., 0.018 inch wire systems, 0.035 inch wire systems), neural, urology, and/or AAA (abdominal aortic aneurysm) applications. In some embodiments, the tube-shaped catheter component can be used as an introducer sheath. The tube-shaped catheter component can be used, for example, in any application in which it may be desirable to have a strong, thin-walled catheter component.

In general, the inner diameter, outer diameter, and wall thickness of the tube-shaped catheter component (e.g., sheath 140, hypotube 160, midshaft 150, distal outer 170, distal inner 180) can be varied as desired. In some embodiments, however, it may be desirable for the tube-shaped catheter component to be relatively thin because, for example, this can reduce the profile of the device. For example (e.g., in 0.014 inch wire systems), the tube-shaped catheter component can have a wall thickness of about 0.005 inch or less (e.g., about 0.004 inch or less, about 0.0035 inch or less, about 0.003 inch or less, about 0.0025 inch or less, about 0.002 inch or less, about 0.0015 inch or less, about 0.001 inch or less). Typical values for the inner diameter of the tube-shaped catheter component are from about 0.02 inch to about 0.035 inch (e.g., from about 0.022 inch to about 0.033 inch), and typical values for the outer diameter of the tube-shaped catheter component are from about 0.02 inch to about 0.043 inch (e.g., from about 0.028 inch to about 0.04 inch).

While the dimensions of hypotube 160 can be varied depending upon the intended use, hypotube 160 usually has an outer diameter of from about 0.02 inch to about 0.03 inch (e.g., about 0.0236 inch, about 0.0264 inch) and a wall thickness of about 0.003 inch or greater.

In general, sheath 140 can have a wall thickness of about 0.005 inch or less (e.g., about 0.004 inch or less, about 0.0035 inch or less, about 0.003 inch or less, about 0.0025 inch or less, about 0.002 inch or less, about 0.0015 inch or less, about 0.001 inch or less). Typical values for the inner diameter of sheath 140 are from about 0.020 inch to about 0.180 inch (e.g., from about 0.020 inch to about 0.030 inch, from about 0.022 inch to about 0.0265 inch), and typical values for the outer diameter of sheath 140 are from about 0.015 inch to about 0.180 inch (e.g., from about 0.025 inch to about 0.035 inch, from about 0.028 inch to about 0.034 inch, from about 0.028 inch to about 0.032 inch). Sheath 140 generally has a length from about 0.100 inch to about 60 inches (e.g., about 44 inches).

Midshaft 150 usually has an outer diameter of from about 0.015 inch to about 0.180 inch (e.g., from about 0.025 inch to about 0.035 inch, from about 0.030 inch to about 0.034 inch, about 0.034 inch) and an inner diameter of from about 0.020 inch to about 0.180 inch (e.g., from about 0.020 inch to about 0.030 inch, about 0.0265 inch). Midshaft 150 usually has a wall thickness of about 0.003 inch or less, and/or about 0.001 inch or more. In certain embodiments, the inner diameter and/or outer diameter of midshaft 150 can be tapered. Generally, midshaft 150 has a length from about four centimeters to about 25 centimeters (e.g., about ten centimeters).

Distal outer 170 generally has an outer diameter from about 0.01 5 inch to about 0.180 inch (e.g., from about 0.030 inch to about 0.036 inch), and an inner diameter from about 0.020 inch to about 0.180 inch (e.g., from about 0.020 inch to about 0.040 inch). In some embodiments, the inner and outer diameters of distal outer 170 taper (decrease going from the proximal end of distal outer 170 to the distal end of distal outer 170). As an example, the proximal end of distal outer 170 can have an outer diameter of 0.0357 inch and an inner diameter of about 0.0283 inch, and the distal end of distal outer 170 can have an outer diameter of about 0.0321 inch and an inner diameter of about 0.0263 inch. In certain embodiments, distal outer 170 is untapered (e.g., with an outer diameter of from about 0.035 inch to about 0.04 inch, such as about 0.037 inch, and an inner diameter of from about 0.0275 inch to about 0.0325 inch, such as about 0.0296 inch). Distal outer 170 typically has a wall thickness of about 0.003 inch or less (e.g., about 0.0027 inch) and/or about 0.001 inch or more. Generally, distal outer 170 has a length from about ten centimeters to about 40 centimeters (e.g., about 21.5 centimeters).

Usually, distal inner 180 has an outer diameter of from about 0.015 inch to about 0.180 inch (e.g., from about 0.015 inch to about 0.180 inch, from about 0.020 inch to about 0.024 inch, from about 0.022 inch to about 0.023 inch), and an inner diameter of from about 0.015 inch to about 0.023 inch (e.g., from about 0.015 inch to about 0.019 inch, from about 0.022 inch to about 0.023 inch). Distal inner 180 typically has a wall thickness of about 0.003 inch or less. Generally, distal inner 180 has a length of from about ten centimeters to about 40 centimeters (e.g., about 24 centimeters).

Balloon 175 can have a diameter of, for example, at least about one millimeter (e.g., at least about two millimeters, at least about three millimeters). In certain embodiments, balloon 175 has a relatively large diameter (e.g., at least about four millimeters, at least about five millimeters, at least about six millimeters, at least about seven millimeters, at least about eight millimeters, at least about nine millimeters, at least about 10 millimeters, at least about 11 millimeters, at least about 12 millimeters, at least about 20 millimeters, at least about 30 millimeters, at least about 40 millimeters).

In general, balloon 175 can be of any desired shape and size (e.g., a coronary balloon, an aortic balloon, a peripheral balloon, a reperfusion balloon, an endoscopy balloon, a urology balloon, and a neurology balloon). In certain embodiments, a coronary balloon can have a diameter of from about 1.5 millimeters to about six millimeters. In some embodiments, a peripheral balloon can have a diameter of from about three millimeters to about 12 millimeters. In certain embodiments, an endoscopy and/or urology balloon can have a diameter of from about four millimeters to about 40 millimeters. In some embodiments, a neurology balloon can have a diameter of from about 1.5 millimeters to about five millimeters.

The strength of the tube-shaped catheter component (e.g., sheath 140, hypotube 160, midshaft 150, distal outer 170, distal inner 180) can generally be varied as desired. But, in certain embodiments, it can be desirable for a tube-shaped catheter component to be relatively strong (e.g., strong enough to withstand the inflation fluid pressure). In some embodiments, it can be desirable for sheath 140 to be strong because this can enhance the ability of sheath 140 to reinforce hypotube 160. Parameters that can be used to measure the strength of a tube-shaped catheter component include, for example, load at break, tensile strength and hoop stress.

In general, the load at break of the tube-shaped catheter component (e.g., sheath 140, hypotube 160, midshaft 150, distal outer 170, distal inner 180) can be varied as desired. Typically, the load at break for the tube-shaped catheter component is at least about two pounds (e.g., at least about three pounds, from about three pounds to about five pounds, from about three pounds to about four pounds). As referred to herein, the load at break of a tube-shaped catheter component is determined as follows. The tube-shaped catheter component is bonded (e.g., heat shrunk) to a wire (e.g., a copper wire with a silver coating), and a longitudinal strain is applied to the wire to reduce the diameter of the wire, thereby removing the tube-shaped catheter component from the wire. Opposite ends of an about three inch long sample of the removed tube-shaped catheter component are placed in grips that are about two inches apart from each other. The grips are pulled apart at a strain rate of about three inches per minute until the tube-shaped catheter component breaks, and the load on the sample as the tube-shaped catheter component breaks is the load at break.

In certain embodiments, the tube-shaped catheter component (e.g., sheath 140, hypotube 160, midshaft 150, distal outer 170, distal inner 180) has a tensile strength of at least about 21,000 pounds per square inch (psi) (e.g., at least about 22,500 psi, at least about 25,000 psi, at least about 27,500 psi, at least about 30,000 psi). As referred to herein, the tensile strength of a tube-shaped catheter component is determined by dividing the load at break of the tube-shaped catheter component by the cross-sectional area of the tube-shaped catheter component, where the cross-sectional area of the tube-shaped catheter component is equal to $\pi(R_o^2-R_i^2)$.

In certain embodiments, the tube-shaped catheter component (e.g., sheath 140, hypotube 160, midshaft 150, distal outer 170, distal inner 180) has a hoop stress of at least about 3300 psi (e.g., at least about 3500 psi, at least about 3750 psi, at least about 4000 psi, at least about 4250 psi, at least about 4500 psi, at least about 4750 psi, at least about 5000 psi). As referred to herein, the hoop stress of a tube-shaped catheter component is equal to $P(R_i^2+R_o^2)/(R_o^2-R_i^2)$, where P is the burst pressure of the tube-shaped catheter component.

In general, the burst pressure of the tube-shaped catheter component (e.g., sheath 140, hypotube 160, midshaft 150, distal outer 170, distal inner 180) can be varied as desired. Typically, the tube-shaped catheter component has a burst pressure of at least about 300 psi (e.g., at least about 400 psi, from about 400 psi to about 700 psi, from about 500 psi to about 600 psi). As referred to herein, the burst pressure of a tube-shaped catheter component refers to the internal pressure at which the tube-shaped catheter component bursts. The burst pressure of a tube-shaped catheter component is determined by measuring the internal pressure of the tube-shaped catheter component as the tube-shaped catheter component (in the case of a hypotube sheath, after being removed from the hypotube) is inflated at a rate of two psi per second with a 10 second hold at every 50 psi interval until the tube-shaped catheter component bursts.

The burst diameter ($D_{burst}$) of the tube-shaped catheter component (e.g., sheath 140, hypotube 160, midshaft 150, distal outer 170, distal inner 180) can also be varied as desired. In certain embodiments, the tube-shaped catheter component has a burst diameter of at least about 0.02 inch (e.g. at least about 0.025 inch, at least about 0.03 inch). As referred to herein, the burst diameter of a tube-shaped catheter component is the outer diameter of the tube-shaped catheter component at burst. The burst diameter of a tube-shaped catheter component is determined by measuring the diameter of the tube-shaped catheter component as the tube-shaped catheter component is inflated at a rate of two psi per second with a 10 second hold at every 50 psi interval until the tube-shaped catheter component bursts. The diameter is measured using a hand held micrometer snap gauge during the 10 second hold periods.

In some embodiments, the change in distention of the tube-shaped catheter component (e.g., sheath 140, hypotube 160, midshaft 150, distal outer 170, distal inner 180) is less than about 0.003 inch (e.g., less than about 0.002 inch, from about 0.001 inch to about 0.002 inch).

As referred to herein, the change in distention of a tube-shaped catheter component is equal to $D_{burst}-D_{initial}$, where $D_{initial}$ is the outer diameter of the tube-shaped catheter component prior to inflation.

In some embodiments, the tube-shaped catheter component (e.g., sheath 140, hypotube 160, midshaft 150, distal outer 170, distal inner 180) can have certain additional properties. For example, in certain embodiments, the tube-shaped catheter component has a post buckle fracture tensile strength of at least about 6500 psi (e.g., at least about 7000 psi, at least about 7500 psi, at least about 8000 psi). As referred to herein, the post buckle fracture tensile strength of a tube-shaped catheter component is determined by dividing the post buckle fracture load at break of the tube-shaped catheter component by the cross-sectional area of the tube-shaped catheter component, where the cross-sectional area of the tube-shaped catheter component is equal to $\pi(R_o^2-R_i^2)$.

In general, the post buckle fracture load at break of the tube-shaped catheter component (e.g., sheath 140, hypotube 160, midshaft 150, distal outer 170, distal inner 180) can be varied as desired. Typically, the post buckle fracture load at break for the tube-shaped catheter component is at least about one pound (e.g., at least about two pounds, from about two pounds to about five pounds, from about two pounds to about four pounds). As referred to herein, the post buckle fracture load at break of a tube-shaped catheter component is determined as follows. Opposite ends of a sample having a length of about 3.5 inches and formed of the tube-shaped catheter component bonded to a hypotube are placed in grips that are about two inches apart from each other. The grips are compressed until the distance between the grips is about 0.3 inch at a rate of about six inches per minute to buckle the sample.

The buckled sample is removed from the grips and straightened so that the hypotube is broken in two separate pieces with each piece of the hypotube still being bonded to the tube-shaped catheter component. Opposite ends of the sample are placed in the grips (two inches apart) and pulled apart at a strain rate of about three inches per minute until the tube-shaped catheter component breaks. The load on the sample as the tube-shaped catheter component breaks is the post buckle fracture load at break.

Typically, the tube-shaped catheter component (e.g., sheath 140, hypotube 160, midshaft 150, distal outer 170, distal inner 180) is formed of a polymer, such as a thermoplastic elastomer (e.g., a heat shrinkable polymer). Examples of polymers include polyamides (e.g., nylons), copolymers of polyamides (e.g., nylon-polyether copolymers), polyesters (e.g., polyethylene terephthalate (PET) polymers, polybutylene terephthalate (PBT) polymers), copolymers of polyesters, polyetheretherketones (PEEKs), polyurethanes, polyethylenes, polypropylenes, copolymers and ionomers of ethylene, copolymers and ionomers of polypropylene, polystyrenes and copolymers of polystyrenes. Examples of commercially available polyesters include the Selar PT family of polymers (e.g., Selar PT 8307, Selar PT4274, Selar PTX280), which are commercially available from E. I. DuPont de Nemours (Wilmington, Del.), the Cleartuf family of polymers (e.g., Cleartuf 8006), which are commercially available from M&G Polymers (Apple Grove, W.V.), the Traytuf family of polymers (e.g., Traytuf 1006), which are commercially available from the Shell Chemical (Houston, Tex.), the Melinar family of polymers, commercially available from E. I. DuPont de Nemours (Wilmington, Del.), the Celanex family of polymers, commercially available from Ticona (Summit, N.J.), the Riteflex family of polymers, commercially available from Ticona (Summit, N.J.), the Hytrel family of polymers (e.g., Hytrel 5556, Hytrel 7246, Hytrel 4056), commercially available from E. I. DuPont de Nemours (Wilmington, Del.), the Arnitel family of polymers (e.g., Arnitel EM630), commercially available from DSM (Erionspilla, Ind.). Examples of commercially available polyamides include Nylon 12, commercially available from Atofina (Philadelphia, Pa.), Nylon 6, commercially available from Honeywell (Morristown, N.J.), Nylon 6/10, commercially available from BASF (Mount Olive, N.J.), Nylon 6/12, commercially available from Ashley Polymers (Cranford, N.J.), Nylon 11, Nylon MXD-6, and the Grivory family of polymers, commercially available from EMS (Sumter, S.C.), the Grilamid® family of polymers (e.g., Grilamid L25, Grilamid L20), commercially available from EMS (Sumter, S.C.), the Vestamid family of polymers (e.g., Vestamid L2101F), commercially available from Daicel-Degussa Ltd., and the PEBAX® family of polymers (e.g., PEBAX 5533, PEBAX 2533, PEBAX 7033), commercially available from Atofina (Philadelphia, Pa.), the Trogamid family of polyamides from Daicel-Degussa, Cristamid MS1100 from Atofina (Philadelphia, Pa.), and Vestamid L2101F nylon 12 from Degussa AG. An example of a commercially available polyethylene is Marlex 4903 high density polyethylene from Phillips 66 (Bartlesville, Okla.).

FIGS. 3A and 3B show a cross-sectional view of an alternate embodiment of a balloon catheter 200, commonly referred to as an over-the-wire catheter. Catheter 200 includes a tip area 202, an inflatable balloon 204 having a waist portion 205, and a shaft portion 206 which extends to the proximal end 208 of the catheter. Shaft portion 206 is attached at its proximal end 207 to a hub assembly 210. Shaft portion 206 includes an outer tube 212 and an inner tube 214 located coaxially within outer tube 212. In some embodiments, outer tube 212 is formed of two tubes, a proximal outer tube and a distal outer tube. An annular lumen 215 is defined between outer tube 212 and inner tube 214. Inner tube 214 runs the entire length of the catheter and defines a central lumen 220, disposed to receive a guidewire. At its distal end 222, outer tube 212 is necked down slightly to mate with waist portion 205. In certain embodiments catheter 200 can include a hypotube as a tube-shaped catheter component at proximal end 207 of shaft portion 206. Examples of such commercially available balloon catheters include the NC Ranger® family of balloon catheters (Boston Scientific-SciMed, Maple Grove, Minn.).

Generally, outer tube 212 has an outer diameter of from about 0.015 inch to about 0.180 inch (e.g., from about 0.030 inch to about 0.034 inch), and an inner diameter of from about 0.015 inch to about 0.180 inch (e.g., from about 0.015 inch to about 0.060 inch). Usually, the proximal outer tube of outer tube 212 has an outer diameter of from about 0.030 inch to about 0.050 inch (e.g., about 0.042 inch) and an inner diameter of from about 0.020 inch to about 0.050 inch (e.g., about 0.035 inch). The proximal end of the distal outer tube of outer tube 212 typically has an outer diameter of from about 0.030 inch to about 0.060 inch (e.g., about 0.043 inch) and an inner diameter of from about 0.020 inch to about 0.060 inch (e.g., about 0.037 inch). The distal end of the distal outer tube of outer tube 212 typically has an outer diameter of from about 0.020 inch to about 0.060 inch (e.g., about 0.037 inch) and an inner diameter of from about 0.020 inch to about 0.050 inch (e.g., about 0.032 inch). Outer tube 212 usually has a wall thickness of about 0.040 inch or less, and about 0.001 inch or more (e.g., about 0.003 inch). Generally, outer tube 212 has a length of from about 30 centimeters to about 180 centimeters (e.g., about 100 centimeters).

Inner tube 214 typically has an outer diameter of from about 0.015 inch to about 0.180 inch (e.g., from about 0.020 inch to about 0.024 inch, from about 0.022 inch to about 0.023 inch) and an inner diameter of from about 0.015 inch to about 0.180 inch (e.g., from about 0.015 inch to about 0.023 inch, from about 0.015 inch to about 0.019 inch, from about 0.022 inch to about 0.023 inch). Inner tube 214 usually has a wall thickness of about 0.003 inch or less. Generally, inner tube 214 has a length of from about 30 centimeters to about 180 centimeters (e.g., about 100 centimeters).

A tube-shaped component of catheter 200 (e.g., outer tube 212, inner tube 214) generally can have the properties (e.g., load at break, tensile strength, hoop stress, burst pressure, burst diameter, change in distention, post buckle fracture tensile strength, and/or post buckle fracture load at break) noted above, and/or can be formed from the materials noted above.

A tube-shaped catheter component (e.g., sheath 140, hypotube 160, midshaft 150, distal outer 170, distal inner 180, outer tube 212, inner tube 214) can be formed of one layer of material (e.g., a polymer), or of multiple layers of material (e.g., at least two layers, at least three layers, at least four layers, at least five layers, at least six layers, at least seven layers, at least eight layers, at least nine layers, at least ten layers). In some embodiments in which the tube-shaped catheter component is formed of multiple layers of material, the tube-shaped catheter component can have increased strength relative to tube-shaped catheter components formed of one layer of material. In certain embodiments in which the tube-shaped catheter component is formed of multiple layers of different materials, the tube-shaped catheter component can exhibit both good strength and good flexibility.

In certain embodiments in which the tube-shaped catheter component (e.g., sheath 140, hypotube 160, midshaft 150, distal outer 170, distal inner 180, outer tube 212, inner tube 214) is formed of multiple layers of material, one of the layers in a pair of adjacent layers can be formed of a certain type (e.g., grade) of a polymer, and the other layer in the pair can be formed of a different type (e.g., grade) of the same polymer. As an example, in certain embodiments in which the tube-shaped catheter component is formed of multiple layers of material, one of the layers in a pair of adjacent layers can be formed of one type of polyester, and the other layer in the pair can be formed of a different type of polyester. As another example, in some embodiments in which the tube-shaped catheter component is formed of multiple layers of material, one of the layers in a pair of adjacent layers can be formed of one type of polyamide, and the other layer in the pair can be formed of a different type of polyamide.

In certain embodiments in which the tube-shaped catheter component (e.g., sheath 140, hypotube 160, midshaft 150, distal outer 170, distal inner 180, outer tube 212, inner tube 214) is formed of multiple layers of material, the layers in a pair of adjacent layers are formed of different polymers. As an example, in some embodiments, one of the layers in a pair of adjacent layers can be formed of a polyester, and the other layer in the pair can be formed of a polyamide.

In certain embodiments in which the tube-shaped catheter component (e.g., sheath 140, hypotube 160, midshaft 150, distal outer 170, distal inner 180, outer tube 212, inner tube 214) is formed of multiple layers of material (e.g., two layers, three layers, four layers, five layers, six layers, seven layers, eight layers, nine layers, ten layers), some (e.g., all) of the layers can have different flexibilities. For example, a multilayer tube-shaped catheter component can have an outer layer that is more flexible than at least one of the inner layers (e.g., all of the inner layers) of the tube-shaped catheter component. In some embodiments, a multilayer tube-shaped catheter component can have an outer layer that is less flexible than at least one of the inner layers (e.g., all of the inner layers) of the tube-shaped catheter component. Flexibility can be measured as flex modulus, which can be calculated using a three-point bend test with a one inch gauge length and a crosshead speed of about 0.3 inch per minute. In some cases, a multilayer tube-shaped catheter component can have inner and outer layers with relatively low flexibilities (e.g., having a flex modulus of from about 160,000 to about 260,000 psi (e.g., about 200,000 psi), according to the three-point bend test), and a middle layer (between the inner and outer layers) with a relatively high flexibility (e.g., having a flex modulus of from about 30,000 psi to about 90,000 psi (e.g., about 50,000 psi), according to the three-point bend test). In certain embodiments, a multilayer tube-shaped catheter component can have inner and outer layers with relatively high flexibilities (e.g., having a flex modulus of from about 30,000 psi to about 90,000 psi (e.g., about 50,000 psi), according to the three-point bend test), and a layer between the inner and outer layers with a relatively low flexibility (e.g., having a flex modulus of from about 160,000 psi to about 260,000 psi (e.g., about 200,000 psi), according to the three-point bend test).

In some embodiments, the layers in a multilayer tube-shaped catheter component (e.g., sheath 140, hypotube 160, midshaft 150, distal outer 170, distal inner 180, outer tube 212, inner tube 214) can be extruded (e.g., as separate extrusions or as a coextrusion). Examples of extrusion processes are described in U.S. Published Patent Application No. US 2002/0165523 A1. Examples of extrusion processes also are described in co-pending and commonly owned U.S. patent application Ser. No. 10/274,633, filed Oct. 21, 2002 and entitled "Multilayer Medical Device", and co-pending and commonly owned U.S. patent application Ser. No. 10/351, 695, filed Jan. 27, 2003 and entitled "Multilayer Balloon Catheter", both of which are hereby incorporated by reference in their entirety. In certain embodiments, the layers in a multilayer tube-shaped catheter component are joined by, for example, an adhesive. In some cases, the layers in a multilayer catheter are joined by an intermediate adhesive layer. Such layers are disclosed in U.S. patent application Ser. No. 10/351,695.

In general, a tube-shaped catheter component (e.g., sheath 140, hypotube 160, midshaft 150, distal outer 170, distal inner 180, outer tube 212, inner tube 214) can be prepared as desired. In some embodiments, a tube-shaped catheter component can be prepared by applying heat, internal pressure, and a longitudinal strain to a tube of material. In certain embodiments, a tube-shaped catheter component can be prepared by applying heat and internal pressure to a tube of material, without applying a longitudinal strain.

FIGS. 4A-4C show an embodiment of a method for forming a tube-shaped catheter component (e.g., sheath 140, hypotube 160, midshaft 150, distal outer 170, distal inner 180, outer tube 212, inner tube 214) by applying heat, internal pressure, and a longitudinal strain to a tube of material. As shown in FIG. 4A, a tube 300 of material is provided. For example, tube 300 can be formed by extrusion. Tube 300 can be formed of one layer or multiple layers. A longitudinal strain, heat and internal pressure are applied to tube 300. This process is referred to herein as longitudinally stretch-blowing the tube. FIG. 4B shows an intermediate tube 305 formed part way through the longitudinal stretch-blowing process. The longitudinal strain applied to the tube is indicated by the horizontal arrows, and the internal pressure applied to the tube is indicated by the vertical arrows. The longitudinal strain, pressure and temperature are ultimately reduced to provide a longitudinally stretch-blown tube 310 of material having an outer diameter that is smaller than the outer diameter of tube 300 and an inner diameter that is smaller than the inner diameter of tube 300 (FIG. 4C).

In certain embodiments, a hypotube sheath is formed by adding the steps shown in FIGS. 4D and 4E to the process of FIGS. 4A-4C. Referring to FIGS. 4D and 4E, a hypotube 320 is placed within stretch-blown tube 310 (FIG. 4D), and stretch-blown tube 310 is heated so that its inner diameter decreases, resulting in a sheath 330 of component material bonded (e.g., heat shrunk) to hypotube 320 (FIG. 4E).

While an embodiment of a process for forming a tube-shaped catheter component (e.g., sheath 140, hypotube 160, midshaft 150, distal outer 170, distal inner 180, outer tube 212, inner tube 214) using heat, internal pressure, and longitudinal strain has been described, other embodiments are possible. In general, the parameters selected during the process can be varied as desired. As an example, the parameters (e.g., longitudinal strain, pressure, temperature) can be selected so that longitudinally stretch-blown tube 310 of material has an outer diameter that is substantially the same as the outer diameter of tube 300 and an inner diameter that is larger than the inner diameter of tube 300. As another example, the parameters (e.g., longitudinal strain, pressure, temperature) can be selected so that longitudinally stretch-blown tube 310 of material has an outer diameter that is smaller than the outer diameter of tube 300 and an inner diameter that is substantially the same as the inner diameter of tube 300.

Without wishing to be bound by theory, it is believed that there are some general trends that depend upon the values of certain parameters (e.g., longitudinal strain, temperature and pressure) used when longitudinally stretch-blowing the tube. The general trends include the following. For a given tube material and desired dimensions for the intermediate tube, increasing the value of one parameter allows for the use of lower values for one or both of the other parameters. For a given material, pressure and longitudinal strain, increasing the temperature results in an intermediate tube with a larger outer diameter. When the tube-shaped catheter component is a hypotube sheath, the resulting intermediate tube tends to undergo a greater degree of shrinkage during the process of bonding (e.g., heat shrinking) to the hypotube. For a given material, pressure and longitudinal strain, decreasing the temperature results in an intermediate tube with a smaller outer diameter. In the case in which the tube-shaped catheter component is a hypotube sheath, the resulting intermediate tube tends to undergo a smaller degree of shrinkage during the process of bonding (e.g., heat shrinking) to the hypotube. For a given material, temperature and pressure, increasing the longitudinal strain results in an intermediate tube with a smaller inner diameter. When the tube-shaped catheter component is a hypotube sheath, the resulting intermediate tube tends to undergo a smaller degree of shrinkage during the process of bonding (e.g., heat shrinking) to the hypotube. For a given material, temperature and pressure, decreasing the longitudinal strain results in an intermediate tube with a larger inner diameter. In the case in which the component is a hypotube sheath, the resulting intermediate tube tends to undergo a greater degree of shrinkage during the process of bonding (e.g., heat shrinking) to the hypotube. For a given material, temperature and longitudinal strain, increasing the pressure results in an intermediate tube with a larger outer diameter. When the tube-shaped catheter component is a hypotube sheath, the intermediate tube tends to undergo a greater degree of shrinkage during the process of bonding (e.g., heat shrinking) to the hypotube. For a given material, temperature and longitudinal strain, decreasing the pressure results in an intermediate tube with a smaller outer diameter. In the case in which the tube-shaped catheter component is a hypotube sheath, the intermediate tube tends to undergo a smaller degree of shrinkage during the process of bonding (e.g., heat shrinking) to the hypotube.

When longitudinally stretch-blowing a tube of material, the temperature of the material should be sufficient to allow the tube to undergo the desired change in dimensions (e.g., to elongate and/or become thinner). The temperature can be varied from, for example, below the glass transition temperature of the material ($T_g$) from which the tube is formed up to about 0.9 times the melt temperature ($T_m$) of the material from which the tube is formed, where $T_m$ is measured in Kelvin. For example, the temperature used during longitudinal stretch-blowing can be at least about $0.85T_g$ (e.g., from about $0.85T_g$ to about $1.2T_g$, from about $0.85T_g$ to about $1.1T_g$, from about $0.85T_g$ to about $T_g$), where $T_g$ is measured in Kelvin. As referred to herein, the glass transition temperature of a material (e.g., a polymer) is determined according to ASTM D1356, and the melt temperature of a material (e.g., a polymer) is determined according to DIN 16770D2. As an example, Vestamid L2101F nylon 12 (Degussa AG) has a $T_g$ of about 333 K and a $T_m$ of about 518 K, and a temperature of about 318 K can be used for this material during longitudinal stretch-blowing, corresponding to about $0.95T_g$ and about $0.6T_m$.

In embodiments in which a tube-shaped catheter component is formed of a block copolymer material, the glass transition temperature and melt temperature of the material refer to the glass transition temperature and melt temperature of the block within the block copolymer that has the highest glass transition temperature and melt temperature. For example, PEBAX 6333 (Atofina) is a block copolymer that contains blocks of nylon 12, and nylon 12 is the block with the highest glass transition temperature and melt temperature in PEBAX 6333. Thus, as referred to herein, the glass transition temperature and melt temperature of PEBAX 6333 correspond to the glass transition temperature and melt temperature of the nylon 12 blocks in PEBAX 6333. Accordingly, PEBAX 6333 has a $T_g$ of about 333 K and a $T_m$ of about 445 K, and a temperature of about 318 K can be used for this material during longitudinal stretch-blowing, corresponding to about $0.95T_g$ and about $0.7T_m$.

In embodiments in which the tube-shaped catheter component (e.g., sheath 140, hypotube 160, midshaft 150, distal outer 170, distal inner 180, outer tube 212, inner tube 214) is formed of multiple layers and in which at least two of the layers are of different materials (e.g., a nylon (such as an amorphous nylon, a semiaromatic nylon) and a polyester), the glass transition temperature and melt temperature of the tube-shaped catheter component refer to the glass transition temperature and melt temperature of the layer of material in the tube-shaped catheter component that has the highest glass transition temperature and melt temperature. For those materials (e.g., amorphous materials) that do not have a melt temperature, a melt processing temperature ($T_{m(process)}$) is used instead. For example, the glass transition temperature and melt processing temperature of a two-layer tube-shaped catheter component having a layer of PEBAX 6333 and a layer of Grilamid TR55 LX are equal to the glass transition temperature and melt processing temperature of the layer with the higher glass transition temperature and melt processing temperature (i.e., the glass transition temperature (155° C.) and melt processing temperature (240-260° C.) of Grilamid TR55 LX). Accordingly, a temperature of about 145° C. can be used for the above two-layer tube-shaped catheter component during longitudinal stretch-blowing, corresponding to about $0.98T_g$ and about $0.8T_{m(process)}$.

In certain embodiments, the temperature of the material during longitudinal stretch-blowing is not measured directly. For example, during longitudinal stretch-blowing, the material may be present in an oven for a period of time. The temperature of the material can be inferred from the period of time the material spent in the oven and the physical characteristics (e.g., heat capacity, thermal conductivity) of the material. The temperature of the material can also be inferred by comparing the properties of the longitudinally stretch-blown material to those of the longitudinally stretch-blown material achieved under conditions where the temperature of the material during longitudinal stretch-blowing is known. For example, the temperature can be inferred by comparing the properties of a longitudinally stretch-blown material to those of the longitudinally stretch-blown material achieved when the material is held in a constant temperature bath (e.g., constant temperature water bath) during longitudinal stretch-blowing.

The longitudinal strain applied to the tube when longitudinally stretch-blowing the tube should be sufficient to allow the material from which the tube is made to undergo the desired change in dimensions (e.g., to elongate and/or become thinner). Typically, the longitudinal strain is at least about 110% (e.g., at least about 120%, at least about 130%, at least about 140%, at least about 150%, at least about 170%, at least about 200%, at least about 210%, at least about 230%, at least about 260%, at least about 290%, at least about 320%, at least about 350%), where the percent longitudinal strain corresponds to the increase in the length of the tube due to longitudinally stretch-blowing the tube. For example, 150% longitudinal strain refers to the stretch-blown tube having a length that is 1.5 times the length the tube had just before being longitudinally stretch-blown.

The internal pressure of the tube during longitudinal stretch-blowing should be sufficient for the material from which the tube is made to undergo the desired change in dimensions (e.g., to elongate and/or become thinner). Typically, the internal pressure is at least about 50 psi (e.g., at least about 75 psi, at least about 100 psi, at least about 125 psi, at least about 150 psi).

Figure 5A:
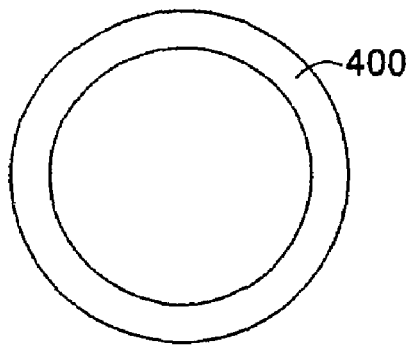
FIGS. 5A-5E are cross-sectional views of another embodiment of a process for forming a tube-shaped catheter component.
Figure 5B:
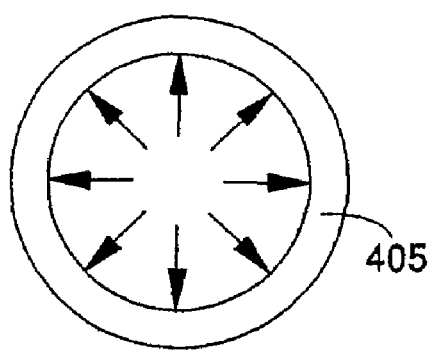
Figure 5C:
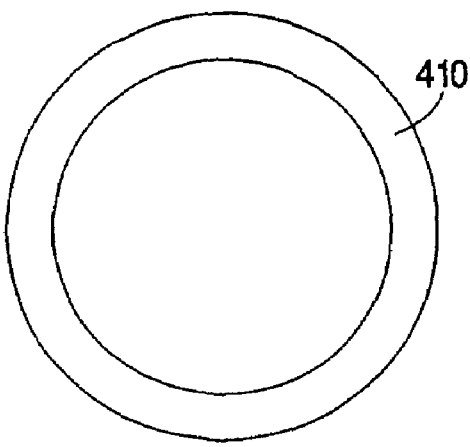

FIGS. 5A-5C show an alternate embodiment for forming a tube-shaped catheter component, in which a tube is pressurized and heated without applying a longitudinal strain. As shown in FIG. 5A, a tube 400 of material is provided. For example, tube 400 can be formed by extrusion. Pressure and heat are applied to tube 400, without applying a longitudinal strain. This process is referred to herein as radially stretch-blowing the tube. FIG. 5B shows an intermediate tube 405 formed part way through the radial stretch-blowing process, in which the pressure applied to the tube is indicated by arrows. The pressure and temperature are ultimately reduced to provide a radially stretch-blown tube 410 of material having an outer diameter that is larger than the outer diameter of tube 400, an inner diameter that is larger than the inner diameter of tube 400, and a wall thickness that is smaller than the wall thickness of tube 400 (FIG. 5C).

Figure 5D:
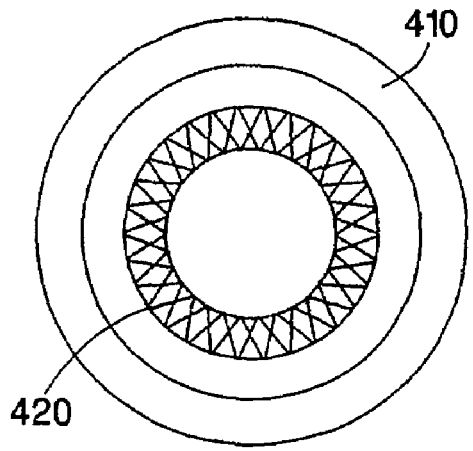
Figure 5E:
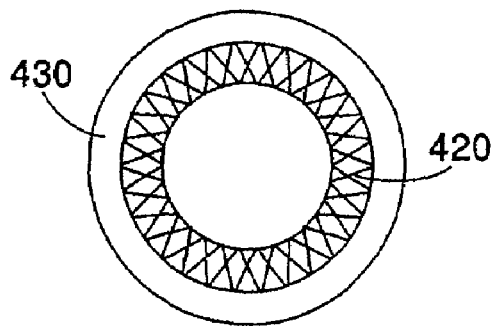

In certain embodiments, a hypotube sheath is formed by adding the steps shown in FIGS. 5D and 5E to the process of FIGS. 5A-5C. In FIGS. 5D and 5E, a hypotube 420 is placed within radially stretch-blown tube 410 (FIG. 5D), and radially stretch-blown tube 410 is heated so that its inner diameter decreases, resulting in a sheath 430 of material bonded (e.g., heat shrunk) to hypotube 420 (FIG. 5E).

When radially stretch-blowing a tube of material, the temperature of the material should be sufficient to allow the tube to undergo the desired change in dimensions (e.g., to expand in diameter and/or become thinner). The temperature can be varied from, for example, below the glass transition temperature of the material ($T_g$) from which the tube is formed up to about 0.9 times the melt temperature ($T_m$) of the material from which the tube is formed, where $T_m$ is measured in Kelvin. For example, the temperature used during radial stretch-blowing can be at least about $0.85T_g$ (e.g., from about $0.85T_g$ to about $1.2T_g$, from about $0.85T_g$ to about $1.1T_g$, from about $0.85T_g$ to about $T_g$), where $T_g$ is measured in Kelvin.

In certain embodiments, the temperature of the material during radial stretch-blowing is not measured directly. For example, during radial stretch-blowing, the material may be present in an oven for a period of time. The temperature of the material can be inferred from the period of time the material spent in the oven and the physical characteristics (e.g., heat capacity, thermal conductivity) of the material. The temperature of the material can also be inferred by comparing the properties of the radially stretch-blown material to those of the radially stretch-blown material achieved under conditions where the temperature of the material during radial stretch-blowing is known. For example, the temperature can be inferred by comparing the properties of a radially stretch-blown material to those of the radially stretch-blown material achieved when the material is held in a constant temperature bath (e.g., constant temperature water bath) during radial stretch-blowing.

When radially stretch-blowing a tube of material, the internal pressure of the tube should be sufficient for the material from which the tube is made to undergo the desired change in dimensions (e.g., to expand in diameter and/or to become thinner). Typically, the internal pressure is at least about 50 psi (e.g., at least about 75 psi, at least about 100 psi, at least about 125 psi, at least about 150 psi).

In some embodiments, individual tube-shaped catheter components are formed (e.g., using the methods discussed above), and then are attached to each other. For example, a first tube-shaped catheter component (e.g., a midshaft) can be formed by longitudinal stretch-blowing, and can be joined to a second tube-shaped catheter component (e.g., a distal outer) which has been formed by radial stretch-blowing. In some cases, a first tube-shaped catheter component (e.g., a hypotube sheath) is formed by longitudinal stretch-blowing, and is joined to a second tube-shaped catheter component (e.g., a midshaft) which has also been formed by longitudinal stretch-blowing. In certain embodiments, a first tube-shaped catheter component (e.g., a distal outer) is formed by radial stretch-blowing, and is joined to a second tube-shaped catheter component (e.g., a midshaft) which has also been formed by radial stretch-blowing. In some embodiments, a first tube-shaped catheter component is formed by longitudinal or radial stretch-blowing, and is joined to a second tube-shaped catheter component which has not been formed by either longitudinal or radial stretch-blowing.

The first and second tube-shaped catheter components can be made of the same or of different materials. For example, the first tube-shaped catheter component can include polyethylene terephthalate and polybutylene terephthalate, and/or polyethylene terephthalate and Hytrel®. As another example, the first tube-shaped catheter component can be made of a nylon (e.g., nylon-12, Grilamid TR55, Cristamid® MS1100), while the second tube-shaped catheter component can be made of a polyester (e.g., PEBAX®). As another example, the first tube-shaped catheter component can include a polyamid and a polyamid copolymer, and/or a polyester and a polyester copolymer. The first and second tube-shaped catheter components can both be single-layer tube-shaped catheter components or can both be multilayer tube-shaped catheter components. The first tube-shaped catheter component can be formed of one layer, while the second tube-shaped catheter component can be a multilayer tube-shaped catheter component.

The first and second tube-shaped catheter components can exhibit different properties. The first and second tube-shaped catheter components can have different flexibilities. For example, the first tube-shaped catheter component can have a flexibility of about 30,000 psi to about 90,000 psi (e.g., about 50,000 psi), while the second tube-shaped catheter component can have a flexibility of about 160,000 psi to about 260,000 psi (e.g., about 200,000 psi).

In certain embodiments, the first and second tube-shaped catheter components are joined by a butt or lap welding process. In some embodiments, the first and second tube-shaped catheter components are joined by an adhesive (e.g., urethane).

Figure 6:
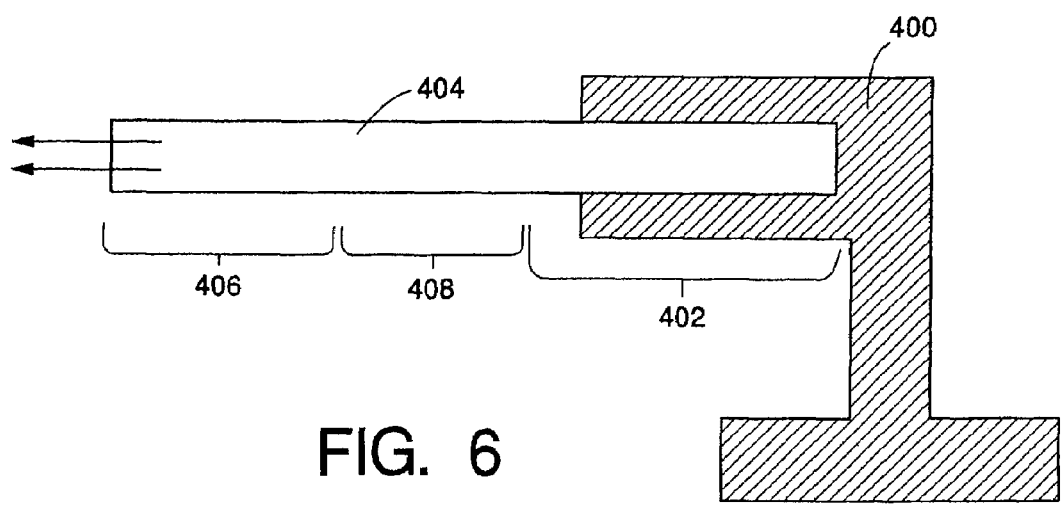
FIG. 6 is a side view of an embodiment of a process for forming a tube-shaped catheter component.

In certain embodiments, a tube-shaped catheter component is formed by longitudinally or radially stretch-blowing a portion of a tube of material. For example, and referring now to FIG. 6, a fixture 400 (e.g., a clamp) is used to hold a first portion 402 of a tube 404 of material in a stationary position. Thereafter, a second portion 406 of tube 404 can be longitudinally or radially stretch-blown. (In FIG. 6, second portion 406 is longitudinally stretch-blown, the longitudinal strain being depicted with arrows.) The stationary portion of the tube is generally unaffected by the stretch-blowing process. A transition region 408 between stationary first portion 402 and stretch-blown second portion 406 experiences an intermediate amount of stretching during the stretch-blowing process.

In some embodiments, a bump extrusion is formed on a tube of material. The portion of the tube including the bump extrusion can then be longitudinally or radially stretch-blown while another portion of the tube is held stationary and is generally unaffected by the stretch-blowing process.

In certain embodiments, an extrusion process can be structured to form a tube of material having the same dimensions (e.g., outer diameter, inner diameter), but a variable polymer orientation, along its length. Thereafter, the tube can be longitudinally or radially stretch-blown. The product of stretch-blowing can be a tube with variable flexibility and strength along its length.

Without wishing to be bound by theory, it is believed that the longitudinal and radial stretch-blowing processes described herein can result in a relatively strong tube-shaped catheter component. In particular, it is believed that the use of a longitudinal strain and/or pressure during the stretch-blowing portion of the process ultimately results in a tube-shaped catheter component that is relatively thin, but that has, for example, a burst pressure and/or load at break that is comparable to those achieved by tube-shaped catheter component preparation processes that result in relatively thick tube-shaped catheter components (e.g., processes in which a longitudinal strain and/or pressure is not used). It is believed that longitudinal and radial stretch-blowing result in relatively thin tube-shaped catheter components that have relatively large tensile strengths and/or relatively large hoop stresses.

As an example, a catheter component material can have a tensile strength ratio of at least about 1.25 (e.g., at least about 1.5, at least about 1.75, at least about two, at least about 2.25). As used herein the tensile strength ratio of a catheter component material is determined by dividing the tensile strength of the material as a tube-shaped catheter component (according to one or more of the procedures described above) by the tensile strength of the material before being longitudinally or radially stretch-blown (e.g., as an extruded tube).

As another example, a catheter component material can have a hoop stress ratio of at least about 1.25 (e.g., at least about 1.5, at least about two, at least about 2.5, at least about three). As used herein, the hoop stress ratio of a catheter component material is determined by dividing the hoop stress of the material as a tube-shaped catheter component (according to the procedure described above) by the hoop stress of the material before being longitudinally or radially stretch-blown (e.g., as an extruded tube).

Without wishing to be bound by theory, it is further believed that the process described herein for bonding a hypotube sheath to a hypotube can result in a hypotube sheath having a polymer chain profile in which the polymer chains are substantially axially oriented (e.g., with the degree of axial orientation generally increasing from the outer radius of the hypotube sheath to the inner radius of the hypotube sheath).

The following examples are illustrative and not intended to be limiting.

EXAMPLES

Tables I and II list average values for certain parameters determined for multiple specimens of different hypotube/hypotube sheath samples. "O.D." refers to the average outer diameter of the hypotube sheaths of the corresponding specimens in units of inches. "I.D." refers to the average inner diameter of the hypotube sheaths of the corresponding specimens in units of inches. "Thickness" refers to the average wall thickness [(outer diameter minus inner diameter)/2] of the hypotube sheaths of the corresponding specimens in units of inches. "Area" refers to the average cross-sectional area (pi multiplied by the difference between the square of the outer radius and the square of the inner radius) of the hypotube sheaths of the corresponding specimens in units of square inches. "Post Load" refers to the average post buckle fracture load at break of the hypotube sheaths of the corresponding specimens in units of pounds. "Post Tensile" refers to the post buckle fracture average tensile strength of the hypotube sheaths of the corresponding specimens units of pounds per square inch. "Load" refers to the load at break of the hypotube sheaths of the corresponding specimens in units of pounds. "Tensile" refers to the average tensile strength of the hypotube sheaths of the corresponding specimens units of pounds per square inch. "Distention" refers to the average change in outer diameter of the hypotube sheaths (outer diameter at burst minus outer diameter prior to inflation) of the corresponding specimens in units of inches. "Diameter" refers to the average burst diameter of the hypotube sheaths of the corresponding specimens in units of inches. "Pressure" refers to the burst pressure the hypotube sheaths of the corresponding specimens in units of psi. "Stress" refers to the burst stress of the hypotube sheaths of the corresponding samples in units of psi.

TABLE I

| Sample | O.D. | I.D. | Thickness | Area | Post Load | Post Tensile |
|---|---|---|---|---|---|---|
| A | 0.0302 | 0.022 | 0.0041 | $3.362 \times 10^{-4}$ | 1.37 | 4075 |
| B | 0.028 | 0.0234 | 0.0023 | $1.857 \times 10^{-4}$ | 1.200 | 6462 |
| C | 0.0296 | 0.0264 | 0.0016 | $1.407 \times 10^{-4}$ | 1.920 | 13642 |
| D | 0.0316 | 0.0264 | 0.0026 | $2.369 \times 10^{-4}$ | 4.420 | 18660 |
| E | 0.03038 | 0.02393 | 0.003225 | $2.751 \times 10^{-4}$ | 4.850 | 17628 |
| F | 0.02891 | 0.02394 | 0.002485 | $2.063 \times 10^{-4}$ | 3.794 | 18391 |
| G | 0.0294 | 0.0264 | 0.0015 | $1.322 \times 10^{-4}$ | 1.48 | 11195 |

TABLE II

| Sample | O.D. | I.D. | Thickness | Distention | Diameter | Load | Tensile | Pressure | Stress |
|---|---|---|---|---|---|---|---|---|---|
| H | 0.0291 | 0.0262 | 0.0015 | 0.0015 | 0.0306 | 3.78 | 31659 | 535 | 5123 |
| I | 0.0282 | 0.0236 | 0.0023 | 0.0012 | 0.0247 | 2.47 | 15129 | 572 | 3197 |
| J | 0.0274 | 0.0232 | 0.0021 | 0.0013 | 0.0244 | 3.62 | 20030 | 529 | 3239 |

Sample A was a Multi-Link Plus™ hypotube (Guidant, Santa Clara, Calif.) modified as follows. A Multi-Link Plus™ hypotube was cut to isolate a specimen formed from the proximal portion of the device containing only the sheath bonded to the hypotube. Three specimens of sample A were tested. The average values of certain parameters determined for the specimens of sample A are listed in Table I.

Sample B was an AVE S7 hypotube (Medtronic AVE, Santa Rosa, Calif.) modified as follows. An AVE S7 hypotube was cut to isolate a specimen formed from the proximal portion of the device containing only the sheath (PEBAX 7233) bonded to the hypotube. Two specimens of sample B were tested. The average values of certain parameters determined for the specimens of sample B are listed in Table I.

Sample C was prepared as follows. An extruded sheath of Vestamid L2101 F Nylon 12 (Degussa AG) having an outer diameter of about 0.0350 inch and an inner diameter of about 0.0276 inch was longitudinally stretch-blown under a longitudinal strain of 220% and an internal pressure of 208 psi. During longitudinal stretch-blowing, the sheath material passed through an 18 inch oven at a temperature of about 63° C. over a period of about 8.9 seconds. It is believed that the sheath material reached a temperature of about 40° C. to about 45° C. during longitudinal stretch-blowing. A 304L stainless steel hypotube having an outer diameter of about 0.0264 inch and an inner diameter of about 0.020 inch was inserted inside the longitudinally stretched and blown sheath, and the sheath was bonded (heat shrunk) to the hypotube by heating to a temperature of about 113° C. for at least 30 minutes. Ten specimens of sample C were tested, and the average values of certain parameters determined for the specimens of sample C are listed in Table I.

Sample D was prepared as follows. An extruded sheath of Vestamid L2101 F Nylon 12 (Degussa AG) having an outer diameter of about 0.0380 inch and an inner diameter of about 0.0270 inch was longitudinally stretch-blown under a longitudinal strain of 190% and an internal pressure of 288 psi. During longitudinal stretch-blowing, the sheath material passed through an 18 inch oven at a temperature of about 68° C. over a period of about 17.1 seconds. It is believed that the sheath material reached a temperature of about 40° C. to about 45° C. during longitudinal stretch-blowing. A 304L stainless steel hypotube having an outer diameter of about 0.0264 inch and an inner diameter of about 0.020 inch was inserted inside the longitudinally stretched and blown sheath, and the sheath was bonded (heat shrunk) to the hypotube by heating to a temperature of about 113° C. for at least about 30 minutes. Five specimens of sample D were tested, and the average values of certain parameters determined for the specimens of sample D are listed in Table I.

Sample E was prepared as follows. An extruded sheath of PEBAX 7233 (Atofina) having an outer diameter of about 0.035 inch and an inner diameter of about 0.024 inch was longitudinally stretch-blown under a longitudinal strain of 150% and an internal pressure of 278 psi. During longitudinal stretch-blowing, the sheath material passed through an 18 inch oven at a temperature of about 68° C. over a period of about 19.5 seconds. It is believed that the sheath material reached a temperature of about 40° C. to about 45° C. during longitudinal stretch-blowing. A 304L stainless steel hypotube having an outer diameter of about 0.0237 inch and an inner diameter of about 0.0175 inch was inserted inside the longitudinally stretched and blown sheath, and the sheath was bonded (heat shrunk) to the hypotube by heating to a temperature of about 113° C. for at least about 30 minutes. Five specimens of sample E were tested, the average values of certain parameters determined for the specimens of sample E are listed in Table I.

Sample F was prepared as follows. An extruded sheath of 95% Vestamid L2101 F Nylon 12 (Degussa AG)/5% PEBAX 7233 (Atofina) having an outer diameter of about 0.0340 inch and an inner diameter of about 0.0240 inch was longitudinally stretch-blown under a longitudinal strain of 150% and an internal pressure of 268 psi. During longitudinal stretch-blowing, the sheath material passed through an 18 inch oven at a temperature of about 68° C. over a period of about 19.5 seconds. It is believed that the sheath material reached a temperature of about 40° C. to about 45° C. during longitudinal stretch-blowing. A 304L stainless steel hypotube having an outer diameter of about 0.0237 inch and an inner diameter of about 0.0175 inch was inserted inside the longitudinally stretched and blown sheath, and the sheath was bonded (heat shrunk) to the hypotube by heating to a temperature of about 113° C. for about 30 minutes. Five specimens of sample F were tested, and the average values of certain parameters determined for the specimens of sample F are listed in Table I.

Sample G was prepared as follows. An extruded sheath of PEBAX 6333 (Atofina) having an outer diameter of about 0.034 inch and an inner diameter of about 0.0280 inch was longitudinally stretched and blown under a longitudinal strain of 155% and an internal pressure of 145 psi. During longitudinal stretch-blowing, the sheath material passed through an 18 inch oven at a temperature of about 68° C. over a period of about 18.9 seconds. It is believed that the sheath material reached a temperature of about 40° C. to about 45° C. during longitudinal stretch-blowing. A 304L stainless steel hypotube having an outer diameter of about 0.0264 inch and an inner diameter of about 0.020 inch was inserted inside the longitudinally stretched and blown sheath, and the sheath was bonded (heat shrunk) to the hypotube by heating to a temperature of about 113° C. for at least about 30 minutes. Five specimens of sample G were tested, and the average values of certain parameters determined for the specimens of sample G are listed in Table I.

Sample H was prepared as follows. An extruded sheath of Vestamid L2101 F Nylon 12 (Degussa AG) having an outer diameter of about 0.0380 inch and an inner diameter of about 0.0320 inch was longitudinally stretched and blown under a longitudinal strain of 220% and an internal pressure of 142 psi. During longitudinal stretch-blowing, the sheath material passed through an 18 inch oven at a temperature of about 63° C. over a period of about 8.9 seconds. It is believed that the sheath material reached a temperature of about 40° C. to about 45° C. during longitudinal stretch-blowing. A 304L stainless steel hypotube having an outer diameter of about 0.0264 inch and an inner diameter of about 0.0200 inch was inserted inside the longitudinally stretched and blown sheath, and the sheath was bonded (heat shrunk) to the hypotube by heating to a temperature of about 113° C. for at least about 30 minutes. Five specimens of sample H were tested, and the average values of certain parameters determined for the specimens of sample H are listed in Table II.

Sample I was a Multi-Link Plus™ hypotube (Guidant, Santa Clara, Calif.) modified as follows. A Multi-Link Plus™ hypotube was cut to isolate a specimen formed from the proximal portion of the device containing only the sheath bonded to the hypotube. 10 specimens of sample A were tested. Three specimens of sample I were tested. The average values of certain parameters determined for the specimens of sample I are listed in Table II.

Sample J was AVE S7 hypotube (Medtronic AVE, Santa Rosa, Calif.) modified as follows. An AVE S7 hypotube was cut to isolate a specimen formed from the proximal portion of the device containing only the sheath (PEBAX 7233) bonded to the hypotube. Two specimens of sample J were tested. The average values of certain parameters determined for the specimens of sample J are listed in Table II.

While certain embodiments have been disclosed, the invention is not so limited.

As an example, the tube-shaped catheter components can be used in any desired medical device system, including catheters having various designs, such as guide catheters, dialysis catheters (e.g., Vaxcel® chronic dialysis catheters), non-valved central venous catheters (e.g., Vaxcel® tunneled central venous catheters), valved central venous catheters (e.g., PASV® tunneled central venous catheters) non-valved peripherally inserted central catheters (e.g., Vaxcel® PICC peripherally inserted central catheters), valved peripherally inserted central catheters (e.g., PASV® PICC peripherally inserted central catheters, and Vaxcel® PICC with PASV® valve technology) or valved ports (e.g., PASV® implantable ports) and non-valved ports (e.g., Vaxcel® standard mini and micro implantable access systems) available from Boston Scientific Corp. (Natick, Mass.).

As another example, the tube-shaped catheter component can be used in balloon catheter systems as described above with reference to FIG. 1, but without also including a midshaft. For example, referring to FIG. 1, a similar balloon catheter can be made to balloon catheter 100 but without midshaft 150, by extending the length of hypotube sheath 140 to the proximal end 172 of distal shaft 170. This could be done, for example, without changing the length of hypotube 160 (e.g., without extending distal end 162 of hypotube 160). Such a balloon catheter could potentially offer the advantage, for example, of a reduced profile.

As a further example, the material can be used in other parts of a balloon catheter, such as, for example, to bond outer and inner tubes of a balloon dilation catheter, to form a sheath over various components of an infusion catheter, as part of the material of the balloon of a balloon catheter, as a sheath to connect the catheter forming portion and a hub forming portion of a catheter-hub assembly, to bond a wire to a hypotube, and/or to join two or more hypotubes (e.g., to join a polymer hypotube to a metal hypotube).

As an additional example, and as noted above, the materials and processes can be used in a variety of systems, including medical device systems and medical devices. The materials and/or processes can be used in any system in which it is desirable to bond two or more components together, particularly where it is advantageous to use relatively strong and/or thin materials to provide the bond between the components. Examples of additional systems include electrical systems (to join electrical components), optical systems (e.g., to join fiber optic cables), packaging, and protective covering over pipes used in flow lines.

As yet another example, a tube of a pre-stretch-blown (e.g., extruded) material and/or a tube of a stretch-blown material can have any desired length and/or cross-sectional shape (e.g., circular, square, triangular, rectangular). Moreover, a pre-stretch-blown (e.g., extruded) material and/or a stretch-blown material need not be in the form of a tube. For example, the material(s) can be in the form of a mat or a sheet (e.g., a flat mat, a flat sheet, a partially rolled mat, a partially rolled sheet).

As an additional example, the tube-shaped catheter component can be non-polymeric. For example, the material can be nitinol, glass, or a metal or metal alloy (such as stainless steel or copper wire).

As another example, in some embodiments a catheter can be longitudinally and/or radially stretch-blown. The catheter can be stretch-blown, for example, to a length of from about 30 centimeters to about 180 centimeters (e.g., about 100 centimeters) and/or an outer diameter of from about 0.020 inch to about 0.180 inch (e.g., from about 0.020 inch to about 0.180 inch).

Other embodiments are within the scope of the following claims.

What is claimed is:

1. A component of a balloon catheter, comprising:
   an elongate shaft including a hypotube and a sheath disposed on the hypotube;
   wherein the elongate shaft includes a region that comprises a polyamide, the polyamide having a post buckle fracture tensile strength of at least about 6500 psi, wherein the region of the component is tube-shaped.

2. The component of claim 1, wherein the region that comprises a polyamide includes a first layer and a second layer, the first layer having a different flexibility from the second layer.

3. The component of claim 1, wherein the post buckle fracture tensile strength of the polyamide is at least about 8000 psi.

4. The component of claim 1, wherein the polyamide has a tensile strength of at least about 21,000 psi.

5. The component of claim 1, wherein the polyamide has a hoop stress of at least about 3300 psi.

6. The component of claim 1, wherein the polyamide comprises a copolymer.

7. A tube-shaped portion of a catheter, the tube-shaped portion including a hypotube and a sheath disposed on the hypotube, the sheath including a region that comprises a polyamide, the polyamide having a post buckle fracture tensile strength of at least about 6500 psi.

8. The tube-shaped portion of claim 7, wherein the sheath comprises a first layer and a second layer, the first layer having a different flexibility from the second layer.

9. The tube-shaped portion of claim 7, wherein the post buckle fracture tensile strength of the polyamide is at least about 8000 psi.

10. The tube-shaped portion of claim 7, wherein the polyamide has a tensile strength of at least about 21,000 psi.

11. The tube-shaped portion of claim 7, wherein the polyamide has a hoop stress of at least about 3300 psi.

12. The tube-shaped portion of a catheter of claim 7, wherein the polyamide comprises a copolymer.

13. A balloon catheter, comprising:
   a hypotube;
   a sheath disposed on the hypotube, wherein the sheath includes a polyamide, the polyamide having a post buckle fracture tensile strength of at least about 6500 psi;
   a midshaft coupled to the sheath;
   a distal outer member attached to the midshaft;
   a distal inner member at least partially disposed within the distal inner member; and
   a balloon attached to the distal outer member.

14. A balloon catheter, comprising:
   a hypotube;
   a sheath disposed on the hypotube, the sheath including a material having a post buckle fracture tensile strength of at least about 6500 psi.

15. The balloon catheter of claim 14, wherein the material is selected from the group consisting of polyamides and copolymers of polyamides.

* * * * *

UNITED STATES PATENT AND TRADEMARK OFFICE
CERTIFICATE OF CORRECTION

PATENT NO. : 7,541,077 B2
APPLICATION NO. : 11/929208
DATED : June 2, 2009
INVENTOR(S) : Victor Schoenle et al.

It is certified that error appears in the above-identified patent and that said Letters Patent is hereby corrected as shown below:

Column 22
Line 45, after "about 6500 psi," and insert therefor -- wherein the region of the component is tube-shaped; --.

Signed and Sealed this

Twenty-first Day of July, 2009

JOHN DOLL
*Acting Director of the United States Patent and Trademark Office*